United States Patent [19]

Chen et al.

[11] 4,374,069
[45] Feb. 15, 1983

[54] PROCESS FOR THE PREPARATION OF TRANS-3-FORMYLBUT-2-ENENITRILE

[75] Inventors: Shi-Chow Chen, Edmonton; John M. MacTaggart, both of Edmonton, Canada

[73] Assignee: Alberta Research Council, Edmonton, Canada

[21] Appl. No.: 253,319

[22] Filed: Apr. 13, 1981

Related U.S. Application Data

[62] Division of Ser. No. 113,444, Jan. 21, 1980, Pat. No. 4,361,702.

[51] Int. Cl.³ .......................................... C07C 121/34
[52] U.S. Cl. ................................................. 260/465.4
[58] Field of Search ...................................... 260/465.4

[56] References Cited

U.S. PATENT DOCUMENTS 3,400,122 9/1968 Albrecht et al. ................. 260/465.6

OTHER PUBLICATIONS

Chem. Abstracts 87:167498b.

Primary Examiner—Ethel G. Love
Attorney, Agent, or Firm—Ernest Peter Johnson

[57] ABSTRACT

A process is provided for the preparation of trans-3-formylbut-2-enenitrile (V), a key intermediate in the synthetic pathway leading to trans-zeatin (I) and dihydrozeatin (II), both of which are naturally occurring cytokinins. The process involves a base catalyzed condensation of a dialkyl or cyclic acetal of pyruvaldehyde (III) with acetonitrile to yield the corresponding dialkyl or cyclic acetal of 3-formylbut-2-enenitrile (IV). The reaction proceeds regioselectively to form the favored trans-isomer in good yield. The α,β-unsaturated nitrile thus formed is hydrolyzed under acidic conditions to yield trans-3-formylbut-2-enenitrile (V), which can be easily distilled without contamination of the cis-isomer. The trans-3-formylbut-2-enenitrile can be selectively or exhaustively reduced to form either trans-3-hydroxymethylbut-2-enylamine (VI) or 3-hydroxymethylbutylamine (VII), which compounds can be condensed with 6-chloropurine (IX) by known methods to form trans-zeatin or dihydrozeatin respectively.

6 Claims, 3 Drawing Figures

I  TRANS-ZEATIN

II  DIHYDROZEATIN

III  PYRUVALDEHYDE ACETAL

IV  ACETAL OF 3-FORMYLBUT-2-ENENITRILE

V  TRANS-3-FORMYLBUT-2-ENENITRILE

VI    TRANS-3-HYDROXYMETHYLBUT-2-ENYLAMINE

VII    3-HYDROXYMETHYLBUTYLAMINE

VIII    TRANS-3-HYDROXYMETHYLBUT-2-ENENITRILE

IX    6-CHLOROPURINE

X    TRANS-3-HYDROXYMETHYLBUT-2-ENENITRILE-TERT-BUTYL-DIMETHYLSILYL ETHER

WHERE $R = \begin{matrix} CH_3 & CH_3 \\ | & | \\ Si - C - CH_3 \\ | & | \\ CH_3 & CH_3 \end{matrix}$

XI    TRANS-3-HYDROXYMETHYL-2-ENYLAMINE SULFATE

4,374,069

PROCESS FOR THE PREPARATION OF TRANS-3-FORMYLBUT-2-ENENITRILE

This is a division of application Ser. No. 113,444 filed Jan. 21, 1980, now U.S. Pat. No. 4,361,702.

BACKGROUND OF THE INVENTION

The present invention relates to processes for the production of key intermediates in the synthetic pathway leading to naturally occurring cytokinins, particularly trans-zeatin and dihydrozeatin.

Cytokinins are naturally occurring 6-substituted aminopurines, which are plant hormones known for their biological activity on plant growth. The more important of these effects are the abilities to induce cell division and regulate differentiation in excised plant tissue. Zeatin is one of the most active forms of the cytokinins.

Owing to the difficulty in isolating even minute quantities of the naturally occurring cytokinins, researchers have turned their efforts to investigating synthetic pathways to form biologically active 6-substituted aminopurines. For trans-zeatin, much of the research has been focused on a suitable synthesis of trans-3-hydroxymethylbut-2-enylamine (VI), the highly functionalized unsaturated side chain which can be condensed, by known methods, with 6-chloropurine to form trans-zeatin. In the case of dihydrozeatin (II), the desired side chain is 3-hydroxymethylbutylamine (VII).

Thus far, known methods for the synthesis of trans-3-hydroxymethylbut-2-enylamine fall into one of the following three categories:

1. A multistep synthesis involving an allylic bromination and starting with tiglic acid, see for example G. Shaw et al., J. Chem. Soc. (c), 921, 1966, and D. S. Letham et al., Phytochemistry, 10, 2077, 1971;
2. A multistep synthesis starting from acetone and cyanoacetic acid and involving allylic bromination, see for example D. S. Letham et al., Aust. J. Chem., 22, 205, 1969; and
3. A Gabriel phthalimide synthesis for the selective allylic amination, starting from isoprene or an isoprenoid halide, see for example M. Ohsugi et al., Agr. Biol. Chem., 38, 1925, 1974, R. Mornet et al., Tetrahedron Lett., 167, 1977, J. Corse et al., Synthesis, 618, 1972, and G. Desvages et al., Bull. Soc. Chim. Fr., 3329, 1969.

Generally the methods of the first two categories involve many steps, provide low yields and require the difficult separation of geometric isomers of the $\alpha,\beta$-unsaturated nitrile necessarily produced by an allylic bromination. The third method involves an unstable dibromide intermediate and requires an undesirable recrystallization step in order to separate an intermediate mixture.

By the method described by D. S. Letham et al., Aust. J. Chem., 22, 205, 1969, it is possible to selectively reduce trans-3-hydroxymethylbut-2-enenitrile (VIII) to trans-3-hydroxymethylbut-2-enylamine (VI) using 2-tetrahydropyranyl as a protecting group for the hydroxyl function. It must be pointed out that, on the basis of the present inventors experiences, lithium aluminum hydride reduction of the 2-tetrahydropyranyl ether of hydroxynitrile (VIII), after the procedure of Letham et al., invariably leads to a complex mixture of products, in which saturated amines are found to be main constituents. Otherwise the hydroxynitrile (VIII) can be exhaustively reduced to form 3-hydroxymethylbutylamine (VII). Condensation of the unsaturated or saturated amine with 6-chloropurine, by for example the method of Letham et al., is known to yield the trans-zeatin or dihydrozeatin.

It is therefore an object of the present invention to provide processes for the preparation of the unsaturated amino alcohol (VI) and the saturated amino alcohol (VII), which can then be transformed by known methods to trans-zeatin and dihydrozeatin respectively.

In a process described in U.S. Pat. No. 3,960,923 issued to DeSimone, $\alpha,\beta$-unsaturated nitriles can be prepared by reaction of a ketone and acetonitrile in the presence of a base. However, as reported in a publication by S. A. DiBiase et al., (Synthesis, 629, 1977) and as supported by the poor yield data presented by DeSimone, this base catalyzed condensation fails or gives very poor yields with methyl ketones.

Since the starting material for the synthesis of the desired unsaturated amino alochol (VI) or saturated amino alcohol (VII), using the reaction scheme of DeSimone, is necessarily a methyl ketone, this process is not feasible for an unactivated methyl ketone.

SUMMARY OF THE INVENTION

The inventor has discovered that whereas a methyl ketone such as acetone cannot be satisfactorily condensed with acetonitrile, an acetal of pyruvaldehyde, which is an $\alpha,\alpha$-dialkoxymethyl substituted methyl ketone, can be condensed with acetonitrile with surprisingly good results. The presence of the acetal group has a number of unexpected effects on the condensation reaction.

Firstly, the fact that the reaction proceeds at all suggests that the acetal group has a stabilizing effect on the polarizing carbonyl group of the pyruvaldehyde acetal. Secondly, the acetal group, being a bulky substituent, influences the stereochemistry of the condensation reaction to give the preferred trans configuration in good yield. Thirdly, the acetal group can be hydrolyzed and subsequently reduced to yield the 3-hydroxymethyl functionality in the target intermediates for the synthesis of trans-zeatin (I) and dihydrozeatin (II), namely trans-3-hydroxymethylbut-2-enylamine (VI) and 3-hydroxymethylbutylamine (VII) respectively.

Thus, in accordance with the present invention a pyruvaldehyde acetal is condensed with acetonitrile in the presence of a strong base. Preferably the base is selected from the group consisting of an alkali alkoxide, sodium hydroxide and potassium hydroxide. The reaction proceeds at elevated temperatures, preferably at reflux temperature. Excess acetonitrile is preferably included as the solvent for the reaction.

The base catalyzed condensation product formed is a cis, trans mixture of the corresponding acetal of 3-formylbut-2-enenitrile (IV), a novel product. As mentioned previously, the reaction proceeds regioselectively favouring the trans-isomer.

Broadly stated, the present invention provides a process comprising: reacting a pyruvaldehyde acetal having the general formula

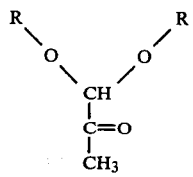

where R is an alkyl, cycloalkyl, substituted alkyl, or alkenyl group having from about 1-10 carbon atoms, or part of a methylene chain in a cyclic acetal of a 5-10 membered ring structure, with acetonitrile in the presence of a strong base at an elevated temperature for a time sufficient to form an acetal of 3-formylbut-2-enenitrile.

In a further aspect of the invention, the acetal of 3-formylbut-2-enenitrile (IV) is acid hydrolyzed, preferably in an aqueous solution of a mineral acid or in an aqueous solution of a mineral acid with a water miscible organic solvent such as methanol, ethanol, or tetrahydrofuran, to form trans-3-formylbut-2-enenitrile (V), also a novel product. Distillation of the crude product yields exclusively the trans-isomer, eliminating the need for separating geometric isomers at any point in the overall synthetic pathway. Presumably the cis-isomer, if formed, further reacts intra- or intermolecularly to form a higher boiling fraction.

The aldehyde group of trans-3-formylbut-2-enenitrile can be selectively reduced in the presence of sodium borohydride in the presence of a suitable solvent such as methanol, ethanol, or tetrahydrofuran to yield trans-3-hydroxymethylbut-2-enenitrile (VIII) without contamination of the saturated alcohol. By masking the allylic hydroxy function with a bulky substituent, the $\alpha,\beta$-unsaturated nitrile (VIII) can be further selectively reduced with lithium aluminum hydride to form trans-3-hydroxymethylbut-2-enylamine (VI). A number of bulky sily groups, such as tert-butyldimethylsilyl group, see for example E.J. Corey et al., J. Am. Chem. Soc., 94, 6190, 1972, have been found to be effective for this purpose. The unsaturated amino alcohol (VI) thus formed can be subsequently condensed with 6-chloropurine (IX) to form trans-zeatin by known methods, see for example G. Shaw et al.

Otherwise, the trans-3-formylbut-2-enenitrile (V) can be exhaustively reduced with a suitable reducing agent to form 3-hydroxymethylbutylamine (VII). The saturated amino alcohol (VII) can be condensed with 6-chloropurine, for example, by the method of Letham et al. to form dihydrozeatin (II). Preferably the reducing agent is a metal hydride-transition metal salt system such as $NaBH_4 \cdot CoCl_2 \cdot 6H_2O$, although a metal hydride such as $LiAlH_4$, or a suitable hydrogenation catalyst in the presence of hydrogen can also be employed.

DESCRIPTION OF THE PREFERRED EMBODIMENT

Figure 1A:
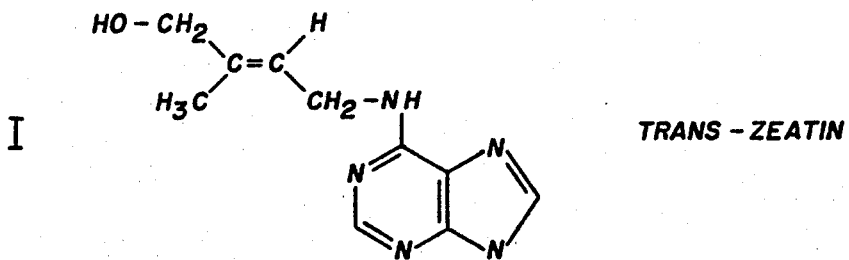
FIGS. 1A and 1B are formula sheets showing structural formulas and names for the compounds referred to in the specification.
Figure 1A:
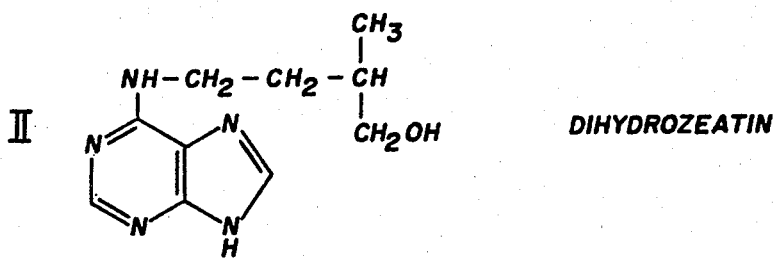
Figure 1A:
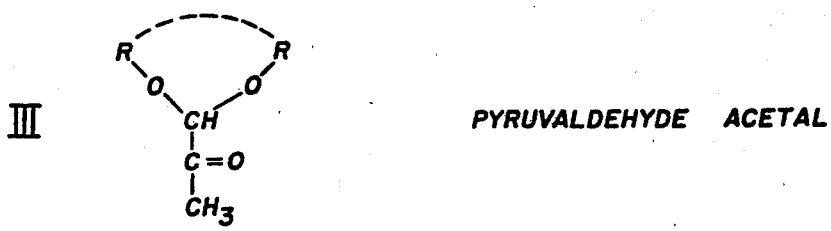
Figure 1A:
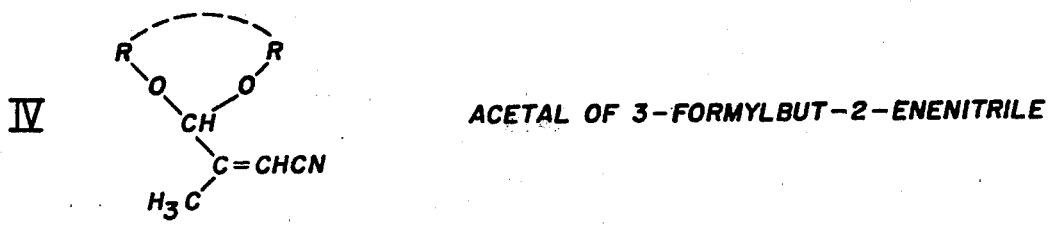
Figure 1A:
Figure 1B:
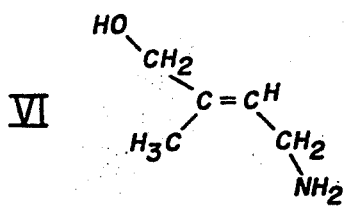
Figure 1B:
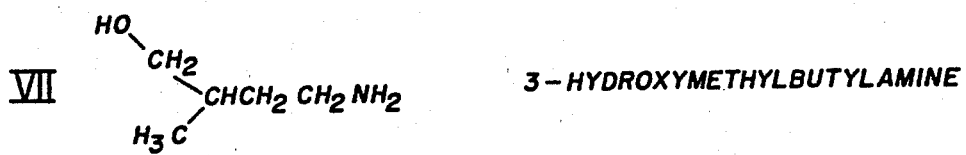
Figure 1B:
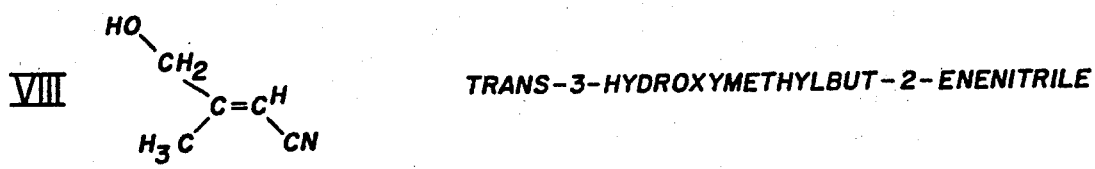
Figure 1B:
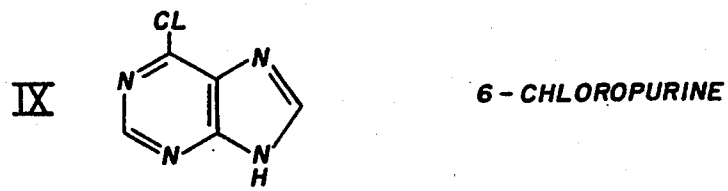
Figure 1B:
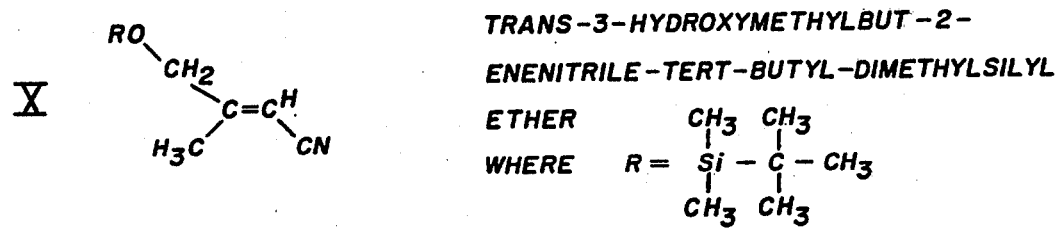
Figure 1B:
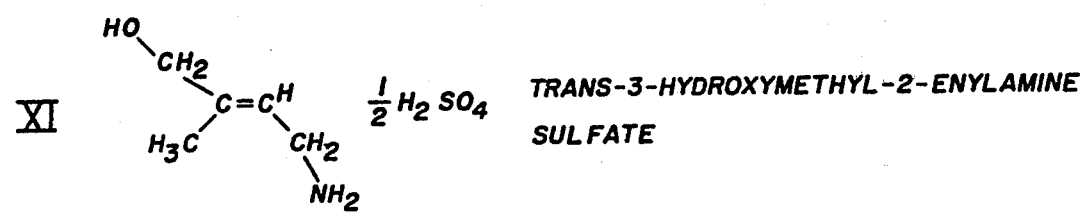
Figure 2:
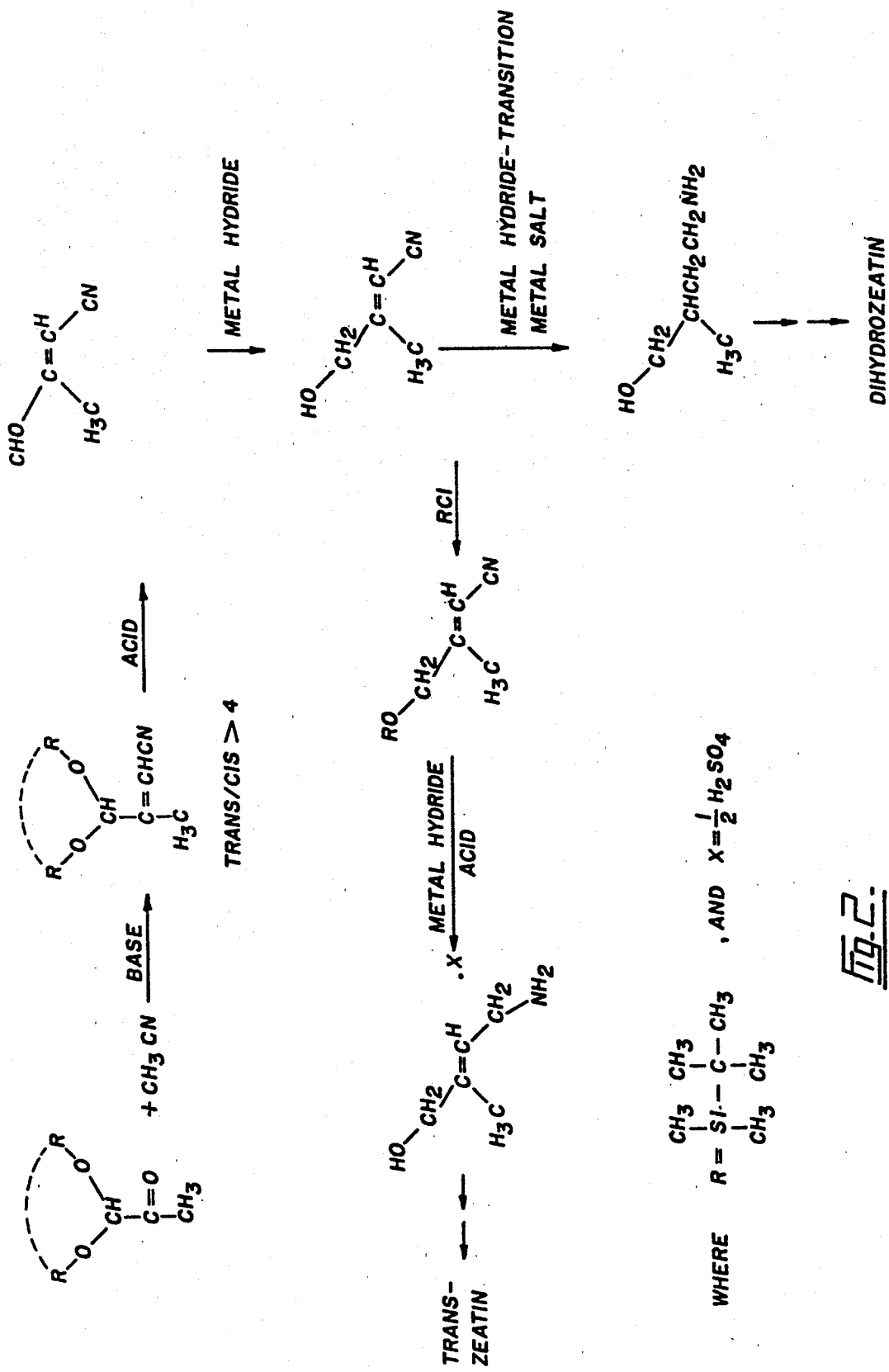
FIG. 2 is a reaction sheet showing an example of the reactions described in the specification.

The present invention involves a base catalyzed condensation of a pyruvaldehyde acetal with acetonitrile to form the corresponding acetal of 3-formylbut-2-enenitrile, which is subsequently hydrolyzed in acidic conditions to form trans-3-formylbut-2-enenitrile. FIG. 2 shows the reactions involved in the present invention starting from pyruvaldehyde dimethyl acetal.

A large number of pyruvaldehyde acetals are suitable as a starting material for the process. Generally the structural formula for the pyruvaldehyde acetal is

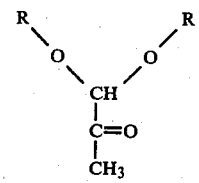

where R is an alkyl, cycloalkyl, substituted alkyl or alkenyl group, having from about 1-10 carbon atoms, or R is a methylene group in a polymethylene chain —$(CH_2)_n$— in a cyclic acetal having a 5-10 membered ring structure. Thus the general formula as given is meant to represent both substituted acetals, such as pyruvaldehyde dimethyl acetal, and cyclic acetals such as 2-acetyl-1,3-dioxan.

A number of pyruvaldehyde acetals are commercially available, however they can also be prepared by reacting 1,3-dihydroxy-2-propanone with monohydric or dihydric alkanols by, for example, the method of S. K. Gupta, J. Org. Chem., 41, 2642, 1976.

The condensation reaction proceeds with stoichiometric quantities of acetonitrile and the pyruvaldehyde acetal, however it is usually desirable to use a large excess of acetonitrile to act as both a reagent and a solvent. The excess acetonitrile can be recovered at the end of the reaction and recycled. Increased yields are generally noted when acetonitrile is used in large excess.

The base used to catalyze the reaction is well known in condensation reactions. Preferably the base is an alkali metal alkoxide such as sodium or potassium methoxide or sodium t-butoxide. Most preferably the alkali alkoxide carries the same alkyl group as the R group in the pyruvaldehyde acetal. For instance, sodium or potassium methoxide are preferred bases for the condensation of acetonitrile with pyruvaldehyde dimethyl acetal.

Sodium or potassium hydroxide may be used in lieu of the alkoxide, however the yield of the hydroxide catalyzed reaction is often inferior.

The amount of base used is preferably in the range of 0.2 to 1.2 moles per mole of pyruvaldehyde acetal. The amount of base used has no significant effect on the final yield of the $\alpha,\beta$-unsaturated nitrile, however the rate of addition of the cyanomethylene anion to the pyruvaldehyde acetal and the subsequent dehydration to give the $\alpha,\beta$-unsaturated nitrile increases with increasing quantities of base. For example, when pyruvaldehyde dimethyl acetal was allowed to react with acetonitrile in the presence of one equivalent of sodium methoxide at reflux temperature for about 2 hours the product mixture yielded about 25% of the tertiary alcohol and 40% of $\alpha,\beta$-unsaturated nitrile. The yield of the alcohol was found to decrease with both an increase in the amount of base, as well as with an increase in the reaction time.

The base may be first introduced in the acetonitrile and the mixture subsequently brought up to reflux temperature. A solution of the pyruvaldehyde acetal in acetonitrile is then added dropwise over about 2-3 hours and the reaction mixture refluxed for about 3-5 hours longer. Alternatively, the pyruvaldehyde acetal, base and acetonitrile may be charged in one reaction vessel and whole refluxed until the completion of the reaction.

The reaction time has been found to be largely variable with the R-substituent of the pyruvaldehyde acetal. The addition of the cyanomethylene anion, which is generated in situ, to the pyruvaldehyde acetal may be completed within about one hour, however an extended reaction time of as much as 10 hours may be required to ensure the dehydration of the primary adduct to give the desired $\alpha,\beta$-unsaturated nitrile. Generally, a pyruvaldehyde acetal which carries a bulky acetal substituent, such as diisopropylacetal or dioxan, requires a longer time for the dehydration of the primary adduct.

At the completion of the reaction, the resultant mixture is washed with water to remove the majority of base and acetamide, a byproduct resulting from the hydration of acetonitrile in the presence of base. Usually, the amount of water used for washing should be less than one tenth of the volume of acetonitrile used for the reaction so that the organic phase remains immiscible with the aqueous phase. The organic phase may be washed again with water. The combined extract is backwashed with low-boiling organic solvent to give additional crop of $\alpha,\beta$-unsaturated nitrile. Evaporation of the solvent under reduced pressure gives a crude liquid product. The combined crude product is distilled at reduced pressure to give a cis,trans mixture of 3-formylbut-2-enenitrile acetal (IV). The separation of the isomeric mixture, which contains about 10-15% of cis form is not necessary since the subsequent transformation of the acetal to the aldehyde produces trans-3-formylbut-2-enenitrile (V) as the main product, which can be easily distilled without contamination of its cis-isomer.

The above formed isomeric mixture of the acetal of 3-formylbut-2-enenitrile (IV) can be hydrolyzed under acidic conditions to remove the acetal group. The acidic solution used is generally an aqueous solution of a mineral or strong organic acid. Alternately the acidic solution can be an aqueous solution of a mineral or suitable strong organic acid together with a water miscible organic solvent to solubilize the starting material. A 5% perchloric acid solution has been found to be suitable for the hydrolysis reaction. Other suitable acids include hydrochloric, sulphuric and oxalic acid.

Acid hydrolysis will proceed at ambient temperatures, however the reaction time may be reduced from about 10 hours to about one hour by hydrolyzing at a reflux temperature.

The product from the acid hydrolysis is extracted with low-boiling organic solvent, such as methylene chloride, to give crude hydrolyzed products. The organic extract is dried with an appropriate drying agent and then concentrated to give crude aldehyde which can be distilled either at atmospheric pressure (182°-187° C. at Edmonton, Alberta, Canada) or at reduced pressure and a low temperature.

The novel aldehyde of this invention, namely trans-3-formylbut-2-enenitrile (V), has been prepared and shown to have the following physical parameters:

b.p. 71°/11 mm Hg; NMR (60 MHz TMS as internal standard in CDCl$_3$ solvent) $\delta$9.73 (singlet, 1H), $\delta$6.40 (quartet, J=1.5 Hz, 1H) and $\delta$2.10 (doublet, J=1.5 Hz, 3H); IR (liquid film) 2843, 2730, 2220, 1705, 1350, 1195, 1027 and 830 cm$^{-1}$. 2,4-dinitrophenylhydrazone derivative, m.p. 276° (decomp.); bis(trans-3-formylbut-2-enenitrile)hydrazone, m.p. 160°-161° C. The liquid aldehyde and the two crystalline hydrazone derivatives gave correct elemental analysis and mass spectral data.

The aldehyde of this invention can be selectively reduced with sodium borohydride in the presence of a low-boiling alcohol as solvent, such as methanol or ethanol, to give trans-3-hydroxymethylbut-2-enenitrile (VIII) without contamination of a saturated alcohol resulting from reduction of the conjugated carbon-carbon double bond. The fact that the conjugated carbon-carbon bond remains intact with NaBH$_4$ reduction suggests that keto-enol tautomerism in the $\alpha,\beta$-unsaturated aldehyde is insignificant. This is clearly due to its extended conjugation with the nitrile group.

The trans-3-hydroxymethylbut-2-enenitrile (VIII) formed by this selective reduction is a natural product found as the alcohol moiety of many plant lipids.

The hydroxynitrile (VIII) thus formed can be further transformed to trans-3-hydroxymethylbut-2-enylamine (VI) in very low yield by the method of Letham et al. Alternatively, it has been found that a number of silyl ethers of trans-3-hydroxymethylbut-2-enenitrile (VIII) can be smoothly transformed to the unsaturated amine (VI) with a LiAlH$_4$ reduction in the presence of diethyl ether solvent. The bulky silyl groups are able to mask the allylic hydroxyl function in the unsaturated nitrile (VIII) from the metal hydride complexation and thus prevent hydride reduction of the carbon-carbon double bond. Suitable silyl reagents include tert-butyldimethylsilyl halides and a range of tri-alkylated silyl halides which can protect the hydroxyl function from metal chelation and resist hydride reduction. The method for their use is disclosed by E. J. Corey et al., J. Am. Chem. Soc., 94, 6190, 1972. The protective silyl group of the protected nitrile (X) is removed by acid hydrolysis, preferably in a solution consisting of 2 normal equivalents of an aqueous mineral acid and water miscible organic solvent, such as methanol or tetrahydrofuran. The hydrolysate is washed with ether or a low-boiling water immiscible organic solvent. The product unsaturated amine (VI) is recovered from the aqueous solution as a salt of an oxo acid or hydrohalide, such as a sulfate or chloride.

It is also possible in accordance with the invention to reduce the $\alpha,\beta$-unsaturated aldehyde (V) to ($\pm$)-3-hydroxymethylbutylamine (VII) with a metal hydride-transition metal salt system or with an appropriate metal hydride, or with the uptake of four moles of hydrogen by means of catalytic hydrogenation. The reduction method used in the invention is preferably a mixed sodium borohydride-metal salt system, such as NaBH$_4$.CoCl$_2$.6H$_2$O, in the presence of a low boiling alcohol. The reduction can be performed by adding five to ten moles excess of sodium borohydride to a 1:1 mole equivalent mixture of cabaltous chloride hexahydrate and the $\alpha,\beta$-unsaturated aldehyde. Preferably however, the aldehyde is first reduced with one mole equivalent of the metal hydride and then one mole equivalent of CoCl$_2$.6H$_2$O is introduced, followed by adding progressively a large excess of sodium borohydride. The use of this metal hydride-transition metal salt reducing agent has been documented by T. Satoh et al., Tetrahedron Lett., 52, 4555, 1969.

The trans-3-hydroxymethylbut-2-enylamine (VI) or its salt (XI) and the 3-hydroxymethylbutyl amine (VII)

can be condensed with 6-chloropurine (IX) to form trans-zeatin (I) and dihydrozeatin (II) respectively. Experimental procedures and conditions have been well documented in the literature and thus will not be disclosed herein. See for example Letham et al., Aust. J. Chem. 22, 205, 1969.

It should be pointed out that the 3-hydroxymethylbutylamine (VII) formed by the above described process has an asymmetric centre. Thus the dihydrozeatin formed therefrom is a racemic mixture. The production of racemic dihydrozeatin and optically pure enantiomers has been reported by T. Fujii et al., Tetrahedron Lett., 30, 3075, 1972.

The following examples further illustrate the nature of the invention and the manner of practicing the same:

EXAMPLE 1

3-Formylbut-2-enenitrile dimethylacetal

A mixture of 600 ml of acetonitrile and 23 g of sodium methoxide was heated to reflux temperature under nitrogen purge and mechanical stirring. To the above mixture was added dropwise, through a pressure equalizing addition funnel, 50 g of pyruvaldehyde dimethylacetal in 200 ml of acetonitrile over a period of three hours. At the completion of addition, the whole mixture was heated to reflux temperature for a further five hours and then allowed to cool to room temperature. The resultant mixture was then shaken twice with a 40 ml portion of water to remove most of the base. The acetonitrile solution was separated and concentrated at 40° C. under reduced pressure of about 15 mm Hg to give crude $\alpha,\beta$-unsaturated nitrile. The combined aqueous extract was backwashed twice with a 50 ml portion of ether to recover an additional crop of the product. The combined crude product was distilled under reduced pressure of 0.05 to 0.5 mm Hg at a distilling head temperature from 32° to 70° C. yielding 41.8 g of $\alpha,\beta$-unsaturated nitrile (70% yield). This product was a colorless liquid which consists of about 11% of cis-3-formylbut-2-enenitrile dimethylacetal and 89% of trans-isomer, as analyzed by gas chromatography.

EXAMPLE 2

3-(1,3-Dioxan-2-yl)but-2-enenitrile

A mixture of 4.2 g of sodium methoxide and 120 ml of acetonitrile was stirred mechanically and heated to reflux under nitrogen purge. To this was then added dropwise 10 g of 2-acetyl-1,3-dioxan in 50 ml of acetonitrile over a period of 2 hours and followed by a 10 hour reflux period. After cooling, the reaction mixture was washed twice with a 10 ml portion of water. The organic phase was then concentrated under reduced pressure at about 40° C. to give the crude $\alpha,\beta$-unsaturated nitrile. The aqueous phase was washed twice with 20 ml portions of ether and the extracts combined, dried, and evaporated to give an additional crop of the product. The combined crude product was distilled under a reduced pressure of 0.2 mm Hg and collected in a boiling range of 72° to 78° C., giving 7.64 g (65% yield) of 3-(1,3-dioxan-2-yl)but-2-enenitrile as a colorless liquid. Both NMR and GLC analyses of the above distillate showed that the liquid consisted of 88% of trans and 12% of the cis-isomer of 3-(1,3-dioxan-2-yl)but-2-enenitrile.

In a separate experiment in which the reflux period was shortened to 5 hours after addition of the acetylacetal, the primary adduct, 3-(1,3-dioxan-2-yl)-3-hydroxybutyronitrile, b.p. 92°–100° C./0.2 mm Hg, was isolated in about 25% yield.

EXAMPLE 3

3-Formylbut-2-enenitrile dimethylacetal

As in example 1, acetals of 3-formylbut-2-enenitrile can also be prepared by directly heating a mixture of an acetal of pyruvaldehyde and sodium methoxide in a large excess of acetonitrile. Thus a mixture of pyruvaldehyde dimethylacetal (50 g), sodium methoxide (11.5 g, 0.5 equivalent) and acetonitrile (600 ml) was heated to reflux temperature for 12 hours. After cooling, the resultant mixture was worked up in a manner similar to that described in example 1, giving 40 g of 3-formylbut-2-enenitrile dimethylacetal.

The results obtained from the condensation of other pyruvaldehyde acetals with acetonitrile are summarized in Table I.

TABLE I

Condensation of Acetonitrile to Pyruvaldehyde Acetals

| Pyruvaldehyde Acetal | Mole Equivalences of NaOCH$_3$ Used | Reaction time (hrs.) | Product | Isolated Yield % (cis:trans) | b.p. C.°/mm Hg |
|---|---|---|---|---|---|
| (CH$_3$O)$_2$CHCOCH$_3$ | 1 | 8 | (CH$_3$O)$_2$CH\C=CHCN / CH$_3$ | 70 (11:88) | 32–41°/0.2 mm |
|  | 0.5 | 16 |  | 69 (12:88) |  |
| (C$_2$H$_5$O)$_2$CHCOCH$_3$ | 1.1 | 16 | (C$_2$H$_5$O)$_2$CH\C=CHCN / H$_3$C | 65 (16:84) | 121–128°/40 mm |
| (i-PrO)$_2$CHCOCH$_3$ | 1.1 | 20 | (i-PrO)$_2$CH\C=CHCN / H$_3$C | 79 (18:82) | 61–65°/0.2 mm |

TABLE I-continued
Condensation of Acetonitrile to Pyruvaldehyde Acetals

| Pyruvaldehyde Acetal | Mole Equivalences of NaOCH$_3$ Used | Reaction time (hrs.) | Product | Isolated Yield % (cis:trans) | b.p. C.°/mm Hg |
|---|---|---|---|---|---|
| (cyclic acetal)–COCH$_2$ | 1.1 | 18 | (cyclic acetal, H$_3$C)C=CHCN | 72 (12:88) | 70–78°/0.2 mm |

EXAMPLE 4 trans-3-Formylbut-2-enenitrile (V)

Forty-three grams of 3-formylbut-2-enenitrile dimethylacetal prepared according to Example 1 or 3 (described above) was dissolved in a methanolic hydrochloric acid solution, prepared by mixing 80 ml of methanol, 500 ml water, and 26 ml of 12N hydrochloric acid. The mixture was heated to reflux for 1 hour. After cooling, the mixture was extracted with three 300 ml portions of methylene chloride. The organic layer was separated and washed with brine, dried over Na$_2$SO$_4$ and evaporated to remove the solvent. The residue was distilled at 70°–73° C. at a reduced pressure of 11 mm Hg to give 23.5 g (81% yield) of trans-3-formylbut-2-enenitrile. The trans-aldehyde was free from the cis-isomer as evidenced from an NMR analysis. The isolated yield of pure trans-$\alpha,\beta$-unsaturated aldehyde, based on its precursor trans-dimethoxymethylbut-2-enenitrile, was 91%.

EXAMPLE 5 trans-3-Hydroxymethylbut-2-enenitrile (VIII)

To a solution of 3.2 g of trans-3-formyl-2-enenitrile in 80 ml of ethanol, cooled in an ice bath and stirred with a magnetic stirrer, was added 1.28 g of NaBH$_4$ in portions over a period of 5 minutes. The mixture was then kept stirred in the ice bath for an additional 10 minutes and subsequently decomposed with 100 ml water. The aqueous ethanol solution was extracted four times with 100 ml portions of ether. The combined ethereal extract was washed with 200 ml of water to remove most of the ethanol. The organic phase was then dried and evaporated to remove the solvent to give practically pure trans-3-hydroxymethylbut-2-enenitrile (VIII) (2.94 g, 90% yield). An analytical sample purified by distillation (72°–73° C./0.15 mm Hg; 68°–71° C./0.25 mm Hg) was identical to that reported in the literature (Letham et al.).

EXAMPLE 6

3-Hydroxymethylbutylamine (VII)

To a solution of 5 g of trans-3-formyl-2-enenitrile in 100 ml of methanol cooled in an ice bath and stirred with a magnetic stirrer, was added 2 g of NaBH$_4$ over 5 minutes. After stirring for an additional 10 minutes in the ice bath, 12.6 g of CoCl$_2$.6H$_2$O was added and left to stir for 5 minutes. To the above mixture was added slowly 8.1 g of NaBH$_4$ over a period of 15 minutes. When the addition was complete, the reaction mixture was left to stir for 2 hours before decomposing with 60 ml of 6 N hydrochloric acid. The resultant mixture was then basified with sodium hydroxide pellets to pH 12 and extracted four times with 150 ml portions of methylene chloride. The combined extracts were dried over K$_2$CO$_3$ and evaporated to remove the solvent, giving 4.0 g of crude 3-hydroxymethylbutylamine (74% yield). The crude amino alcohol had an 60 Hz NMR spectrum in CDCl$_3$ of $\delta$0.9 (doublet, J=6 Hz, 3H), $\delta$1.5 (multiplet, 3H), $\delta$2.7 (multiplet, 2H), $\delta$3.4 (doublet, J=5.5 Hz, 2H) and a D$_2$O exchangeable singlet at around $\delta$3.5 (3H). The product was sufficiently pure for the synthesis of racemic dihydrozeatin by the method of Fujii et al. An additional amount (430 mg) of the crude amino alcohol product, which was less pure than that isolated above, was obtained by continuous extraction of the aqueous solution with ether or methylene chloride.

EXAMPLE 7 trans-3-Hydroxymethyl-2-enenylamine sulfate (XI)

The compound trans-3-hydroxymethylbut-2-enenitrile tert-butyldimethylsilyl ether (X) was prepared in quantitative yield from trans-3-hydroxymethylbut-2-enenitrile and tert-butyldimethylsilyl chloride by the method of E. J. Corey and A. Venkateswarlu, J. Amer. Chem. Soc. 94, 6190, 1972. The compound X had the following physical parameters: b.p. 72°–74° C./0.05 mm Hg; NMR (80 MHz, TMS as an internal standard in CDCl$_3$ solvent) $\delta$0.07 (singlet, 6H), $\delta$0.92 (singlet, 9H), $\delta$1.96 (doublet of triplet, J=1.1 Hz, J=0.85 Hz, 3H), $\delta$4.15 (doublet of quartets, J=2 Hz, J=0.85 Hz, 2H), $\delta$5.53 (eight-line multiplet, J=2 Hz, J=1.1 Hz); IR (liquid film) 2955, 2930, 2220, 1680, 1255, 1120, 840, and 780 cm$^{-1}$.

To a solution of 3 g of the above nitrile (X) in 100 ml of anhydrous ether, cooled and stirred in an ice bath, was added 810 mg of LiAlH$_4$ over 5 minutes. The mixture was stirred 1 hour in an ice bath, 1 hour at room temperature and 1 hour at reflux temperature. The resultant complex was allowed to cool, was decomposed with 2.5 ml of water and then treated with MgSO$_4$ to aid coagulation of the solid. The solid was removed by filtration and washed thoroughly with 100 ml of ether. After evaporating the solvent, 2.6 g of a light yellow liquid product were obtained. Gas chromatographic analysis of the crude product showed it to contain 70% of the desired unsaturated amino alcohol silyl ether. A pure colorless sample obtained by distillation (64°–67° C./0.05 mm Hg) had an NMR spectrum (80 Hz in CDCl$_3$ solvent) of $\delta$0.06 (singlet, 6H), $\delta$0.93 (singlet, 9H), $\delta$1.62 (singlet with fine splitting J=1.4 Hz, 3H), $\delta$1.84 (broad singlet, D$_2$O exchangeable, 2H), $\delta$3.20 (doublet, J=6.8 Hz with fine splitting), $\delta$4.05 (singlet with fine splitting, 2H), $\delta$5.56 (triplet of quartet, J=6.8 Hz, J=1.4 Hz, 1H); an IR (liquid film) of 2955, 2930, 2860, 1670, 1550, 1473, 1465, 1340, 1363, 1255, 1080, 1005, 940, 835, and 773 cm$^{-1}$.

A quantity of 1.8 g of the above prepared crude amino alcohol was dissolved in 20 ml of methanolic sulfuric acid (5% v/v 1 N H₂SO₄ in methanol) and stirred at room temperature for 4 hours. The resultant mixture was washed twice with 30 ml portions of ether. The aqueous layer was separated and evaporated under reduced pressure at 50° C. to yield 1.3 g of a light brown syrup. The liquid product had an NMR spectrum (80 Hz in D₂O) of δ1.74 (singlet, 3H), δ3.7 (doublet, J=7.5 Hz, 2H), δ4.0 (singlet, 2H), δ5.5 (triplet, 7.5 Hz).

The sulfate (XI) could not be easily obtained in a crystalline form, however, it can be used directly for the synthesis of zeatin according to the method of G. Shaw et al., J. Chem. Soc. (c), 921, 1966.

It should be realized that although the present invention has been disclosed with an objective of providing a synthetic pathway to zeatin, one skilled in the art will recognize that the trans-3-formylbut-2-enenitrile (V) product formed herein is a isoprenoid which may have further utility in the synthesis of other natural products or useful chemical building blocks.

Furthermore, while the present invention has been disclosed in connection with the preferred embodiments thereof, it should be understood that there may be other embodiments which fall within the spirit and scope of the present invention as defined by the following claims.

The embodiments of the invention in which an exclusive property or privilege is claimed are defined as follows:

1. trans-3-Formylbut-2-enenitrile having the structure:

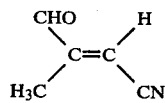

2. The process comprising:

reacting a pyruvaldehyde acetal having the general formula

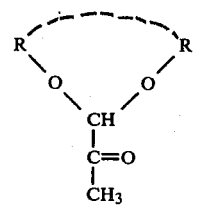

where R is an alkyl, cycloalkyl, substituted alkyl, or alkenyl group having from about 1–10 carbon atoms, or part of a methylene chain in a cyclic acetal of a 5–10 membered ring structure, with acetonitrile in the presence of a strong base at an elevated temperature for a time sufficient to form an acetal of 3-formylbut-2-enenitrile; and hydrolyzing the acetal of 3-formylbut-2-enenitrile in an acidic solution selected from the group consisting of an aqueous mineral acid, an aqueous strong organic acid, an aqueous mineral acid and a water miscible organic solvent, and an aqueous strong organic acid and a water miscible organic solvent, to form a product mixture containing trans-3-formylbut-2-enenitrile.

3. The process as set forth in claim 2 wherein:
the acetal of 3-formylbut-2-enenitrile is a dialkyl acetal of 3-formylbut-2-enenitrile.

4. The process as set forth in claim 2 wherein:
the acetal of 3-formylbut-2-enenitrile is the dimethylacetal of 3-formylbut-2-enenitrile.

5. The process as set forth in claim 2 wherein:
the acetal of 3-formylbut-2-enenitrile is a cyclic acetal of 3-formylbut-2-enenitrile.

6. The process as set forth in claim 2 or 4 wherein the product mixture is distilled to separate trans-3-formylbut-2-enenitrile.

* * * * *